(12) United States Patent
Witham

(10) Patent No.: US 7,048,728 B2
(45) Date of Patent: May 23, 2006

(54) NONINVASIVE MEDICAL INSTRUMENT

(76) Inventor: Richard N. Witham, 709 Ruddiman Dr., North Muskegon, MI (US) 49445

( * ) Notice: Subject to any disclaimer, the term of this patent is extended or adjusted under 35 U.S.C. 154(b) by 411 days.

(21) Appl. No.: 10/133,105

(22) Filed: Apr. 26, 2002

(65) Prior Publication Data
US 2003/0204170 A1 Oct. 30, 2003

(51) Int. Cl.
A61M 25/00 (2006.01)
A61H 7/00 (2006.01)
F16L 55/00 (2006.01)

(52) U.S. Cl. .................. 604/527; 601/137; 15/104.93; 15/104.94

(58) Field of Classification Search ............... 600/585; 604/527, 523; 601/137; 15/110, 111, 104.93, 15/104.94
See application file for complete search history.

(56) References Cited

U.S. PATENT DOCUMENTS

| 874,251 | A | * | 12/1907 | Schelling | 601/114 |
|---|---|---|---|---|---|
| 2,116,864 | A | * | 5/1938 | Fehrenbach | 401/24 |
| 2,641,012 | A | * | 6/1953 | Storrs | 15/144.4 |
| 2,711,731 | A | * | 6/1955 | Krohne | 601/137 |
| 3,103,682 | A | * | 9/1963 | Markle | 15/244.1 |
| 3,521,620 | A | * | 7/1970 | Cook | 600/585 |
| 3,527,208 | A | * | 9/1970 | Hoegerman | 601/136 |
| 3,841,308 | A | * | 10/1974 | Tate | 600/585 |
| 4,667,659 | A | * | 5/1987 | Hayday | 601/137 |
| 4,682,607 | A | * | 7/1987 | Vaillancourt et al. | 600/585 |
| 4,737,153 | A | | 4/1988 | Shimamura et al. | |
| 4,760,845 | A | | 8/1988 | Kovalcheck | |
| 4,763,647 | A | * | 8/1988 | Gambale | 600/434 |
| 4,776,844 | A | | 10/1988 | Ueda | |
| 4,899,741 | A | | 2/1990 | Bentley et al. | |
| 5,016,619 | A | * | 5/1991 | Fitzpatrick | 601/120 |
| 5,020,182 | A | * | 6/1991 | Engel | 15/145 |
| 5,084,022 | A | * | 1/1992 | Claude | 604/164.13 |
| 5,221,257 | A | * | 6/1993 | Rosenbloom et al. | 604/510 |
| 5,368,049 | A | * | 11/1994 | Raman et al. | 600/585 |
| 5,423,848 | A | | 6/1995 | Washizuka et al. | |
| 5,465,733 | A | | 11/1995 | Hinohara et al. | |
| 5,485,948 | A | | 1/1996 | McCrink | |

(Continued)

Primary Examiner—Sharon Kennedy
(74) Attorney, Agent, or Firm—Pauley Petersen & Erickson

(57) ABSTRACT

A noninvasive medical instrument having a core and a flexible outer coil surrounding about the core to form an elongated body. The elongated body has a rounded tip portion, which is preferably burrless, to prevent the noninvasive medical instrument from penetrating or entering a skin surface of a patient. The noninvasive medical instrument of this invention can be used to scratch an irritated skin surface that is otherwise inaccessible due to interference caused by a cast, a prosthetic device or another structural obstruction. If the core is hollow, the noninvasive medical instrument of this invention can be used to deliver fluidic medicine to a likewise inaccessible skin area.

18 Claims, 3 Drawing Sheets

U.S. PATENT DOCUMENTS

| | | | | |
|---|---|---|---|---|
| 5,593,419 A * | 1/1997 | Segar | ................ | 606/194 |
| 5,702,373 A | 12/1997 | Samson | | |
| 5,716,754 A * | 2/1998 | Arnost et al. | ................ | 430/200 |
| 5,730,709 A * | 3/1998 | Sergent | ................ | 601/137 |
| 5,782,811 A * | 7/1998 | Samson et al. | ................ | 604/527 |
| 5,807,279 A * | 9/1998 | Viera | ................ | 600/585 |
| 5,810,027 A * | 9/1998 | Frantzeskakis | ................ | 132/320 |
| 5,827,201 A * | 10/1998 | Samson et al. | ................ | 600/585 |
| 5,947,940 A | 9/1999 | Beisel | | |
| 6,004,330 A | 12/1999 | Middleman et al. | | |
| 6,009,887 A * | 1/2000 | Hertel | ................ | 132/317 |
| 6,130,406 A | 10/2000 | Cheer | | |
| 6,165,292 A | 12/2000 | Abrams et al. | | |
| 6,171,235 B1 | 1/2001 | Konstorum et al. | | |
| 6,183,491 B1 * | 2/2001 | Lulo | ................ | 606/191 |
| 6,261,014 B1 * | 7/2001 | Altobellis et al. | ................ | 401/6 |
| 6,287,326 B1 | 9/2001 | Pecor | | |
| 6,306,105 B1 * | 10/2001 | Rooney et al. | ................ | 600/585 |
| 6,322,534 B1 | 11/2001 | Shkolnik | | |
| 6,432,066 B1 * | 8/2002 | Ferrera | ................ | 600/585 |
| 6,754,929 B1 * | 6/2004 | Fichter | ................ | 15/114 |
| 2001/0010247 A1 | 8/2001 | Snow | | |
| 2001/0034514 A1 * | 10/2001 | Parker | ................ | 604/525 |

* cited by examiner

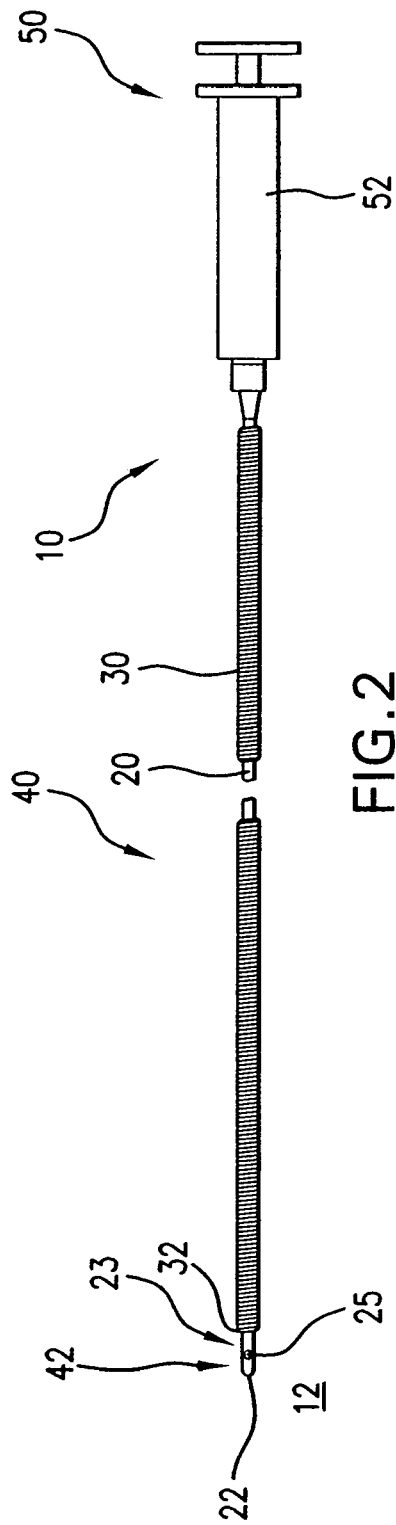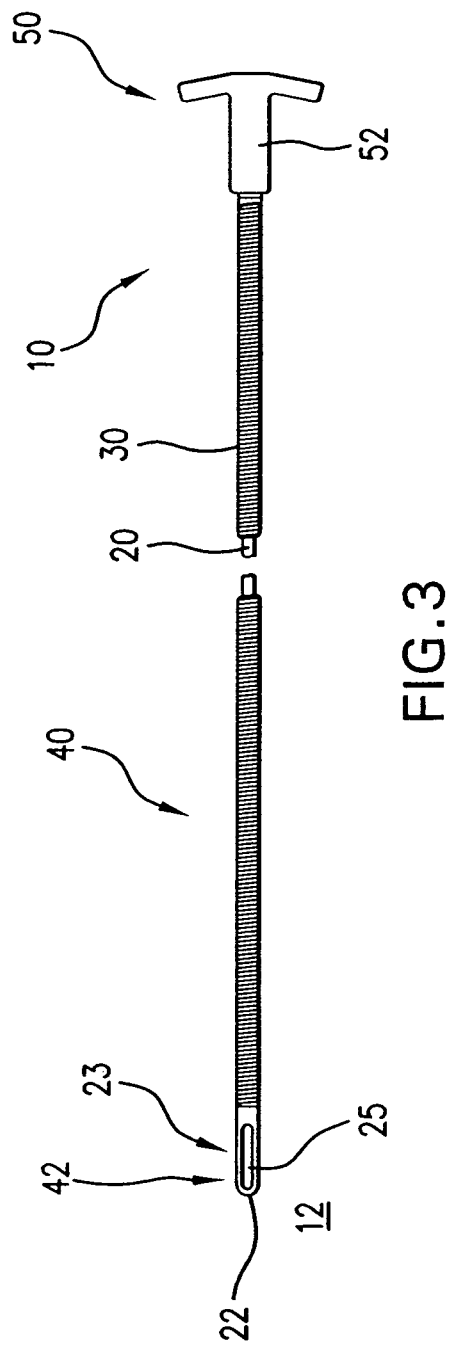

NONINVASIVE MEDICAL INSTRUMENT

BACKGROUND OF THE INVENTION

1. Field of the Invention

This invention relates to a noninvasive medical instrument used to provide therapy to external skin surfaces of a patient, particularly skin surfaces which are difficult to access, such as skin areas covered by a cast or other prosthetic device.

2. Description of Prior Art

Patients, doctors and therapists use many different relatively bulky instruments to access skin areas of patients that are otherwise inaccessible due to interfering casts, prosthetic devices or other similar structures or wound dressings. Many instruments for scratching inaccessible dry and irritated skin surfaces are inappropriate for the intended use. For example, patients often use pencils, rods or other relatively small instruments to position between a cast and an inaccessible skin surface, resulting in dropping the inappropriate instrument into the cast, often requiring removal of the cast to retrieve the inappropriate instrument.

Also, skin surfaces having cuts, abrasions or other skin wounds that require medication can only be accessed by removing a cast.

Other inappropriate instruments, such as coat hangers, sticks and the like, used to provide physical therapy or medicine to such inaccessible areas have sharp edges, points or other structural features that can puncture, cut or otherwise harm a skin surface.

It is apparent that there is a need for a rigid yet flexible instrument that provides a safe abrasive surface for scratching or massaging an inaccessible skin surface. It is apparent that there is a need for a noninvasive medical instrument that can deliver a drug or medicine to an inaccessible cut, abrasion or other skin wound. It is apparent that there is also a need for a noninvasive medical instrument that can carry, deliver or otherwise provide a swab to an inaccessible skin area.

SUMMARY OF THE INVENTION

It is one object of this invention to provide a medical instrument for noninvasive therapy to a skin surface of a patient, for example to scratch areas of the skin which are otherwise inaccessible due to a cast, a prosthetic device or any other interfering structure.

It is another object of this invention to provide a medical instrument that can be used to noninvasively deliver fluidic medicine or to carry a swab to an external skin surface, for example to treat skin areas and/or to apply medicine, such as a topical numbing agent, to skin areas that are otherwise inaccessible, as previously discussed.

It is another object of this invention to provide a method for manufacturing a noninvasive medical instrument.

The noninvasive medical instrument according to this invention is a relatively rigid yet flexible apparatus that can be used to access and provide therapy to otherwise inaccessible skin areas of a patient. As used throughout this specification and in the claims, the term noninvasive is intended to relate to medical instrument 10 not entering the skin surface of a patient.

The above and other objects of this invention are accomplished with a noninvasive medical instrument that has a core and a flexible outer coil wound about the core, to form an elongated body. Because the noninvasive medical instrument of this invention is moved in a reciprocating manner, in one embodiment of this invention it is important for the instrument body to have a rounded tip portion. As used throughout this specification and in the claims, the word rounded is intended to relate to a tip portion that is spherical, partially spherical, generally spherical, non-spherical and/or partially non-spherical, and is also intended to relate to any smooth surface that is burrless, having no pointed, jagged or other irregular structure that would penetrate the skin surface.

In one embodiment of this invention, a suitable rounded tip portion is formed by plasma-arc welding an end of the coil to the core. During the plasma-arc welding process, a bead or globule of welding material hardens and forms the rounded tip portion. To form a more spherical and/or smoother rounded tip portion, during the welding process a ceramic fixture or mold can be positioned relatively close to the tip of the elongated body, so that the welding material conforms to the shape of the ceramic fixture.

In one embodiment of this invention, the core is solid and the coil preferably but not necessarily extends along the elongated body, completely to an end or an end portion of the core.

In another embodiment according to this invention, the core is hollow and the coil extends along the elongated body, preferably but not necessarily stopping short of an end or an end portion of the core. The hollow core forms a passage or channel extending along the elongated body. A tip portion of the core has at least one void that forms communication between the channel and an environment surrounding the rounded tip portion. A fluidic supply can be connected with respect to the hollow core and can be in communication with and deliver fluid to the channel of the hollow core. In one embodiment of this invention, the fluidic supply includes a syringe that can deliver fluid through the channel and each void. The noninvasive medical instrument according to such embodiment of this invention can be used to apply medicine to an otherwise inaccessible area of the skin. For example, the noninvasive medical instrument having the hollow core can be used to apply medicine to a cut, an abrasion or another skin wound which may otherwise be inaccessible.

As used throughout this specification and in the claims, the phrase otherwise inaccessible or the word inaccessible each is intended to relate to a skin area of a patient that cannot be easily accessed by conventional syringes or other medical instruments, for applying medicine to a wounded skin area.

Another embodiment of this invention relates to a method for manufacturing a noninvasive medical instrument. In the manufacturing method, a flexible coil formed by winding and/or coiling is positioned about the core, to form an elongated body. One end of the coil is fixedly secured to the core. A rounded tip portion is formed at an end, an end portion or a free end portion of the elongated body.

In one embodiment of this invention, the coil is plasma-arc welded to the core, to form a rounded and/or burrless structure.

In one embodiment of this invention, the wound coil is formed by controlling deflection of a wire about an arbor. In another embodiment of this invention, the coil is formed by wrapping a wire around a mandrel.

Regardless of whether the core is solid or hollow, the core and the coil form an elongated body that preferably has a rounded tip portion. Thus, the body of either embodiment can be reciprocated to physically scratch an external surface of a skin area which is otherwise inaccessible. The embodiment having the solid core can be used for scratching therapy. The embodiment having a hollow core can be used as a scratching device and/or as a drug or medicine delivery device.

BRIEF DESCRIPTION OF THE DRAWINGS

The above and other objects of this invention are best understood when the specification is read in view of the drawings, wherein:

FIG. 2 is a front view of a noninvasive medical instrument having a hollow core, with a circular through hole forming a void in a wall at a tip portion of the core, according to one embodiment of this invention;

FIG. 3 is a front view of a noninvasive medical instrument having a hollow core, with a through slot forming a void in a wall at a tip portion of the core, according to another preferred embodiment of this invention;

DESCRIPTION OF PREFERRED EMBODIMENTS

Figure 1:
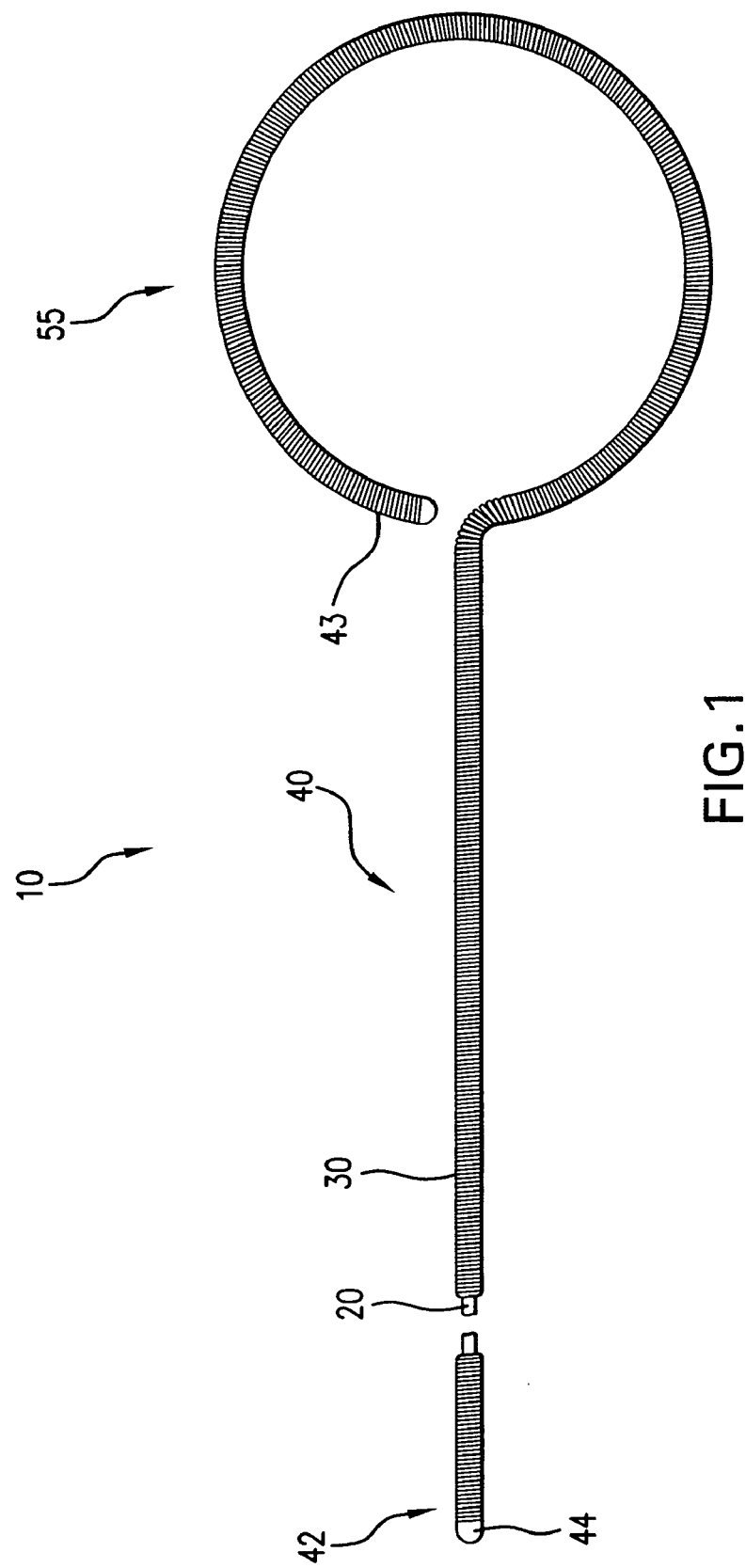
FIG. 1 is a front view of a noninvasive medical instrument having a solid core, according to one embodiment of this invention.

Medical instrument 10 according to this invention, such as in the different embodiments shown in FIGS. 1–3, is preferably a noninvasive medical instrument used to either apply physical therapy to a skin area of a patient or to deliver a fluidic drug or medicine to an inaccessible skin area. For example, medical instrument 10 of this invention can be used to scratch an irritated skin surface which is inaccessible because of an interfering cast, prosthetic device or another structure. As another example, medical instrument 10 of this invention can be used to deliver medicine to a similarly inaccessible skin area.

As shown in FIGS. 1–3, medical instrument 10 comprises core 20 and coil 30, which is preferably an outer coil wound about core 20. Coil 30 can be either tightly or loosely wound about core 20. Core 20 and surrounding coil 30 form overall elongated body 40, which can have any suitable length.

Body 40 preferably forms rounded tip portion 42. Tip portion 42 is preferably burrless, having no pointed, sharp or other structural projection that could puncture a skin surface.

In one embodiment of this invention, end 32 of coil 30 is plasma-arc welded to core 20. In such embodiment, tip portion 42 is formed by resultant bead or globule 44 of welding material. Plasma-arc welding produces a smooth, burrless surface that forms rounded tip portion 42. Other suitable welding processes can be used to secure coil 30 with respect to core 20. However, other welding processes may result in tip portion 42 requiring a further grinding step or other abrasive process step to remove any burr and render tip portion 42 burrless. It is also possible to use a ceramic fixture or other suitable fixture or mold, for example to reduce surface tension in the bead of welding material, to form tip portion 42 into a rounded or smooth configuration.

Figure 4:
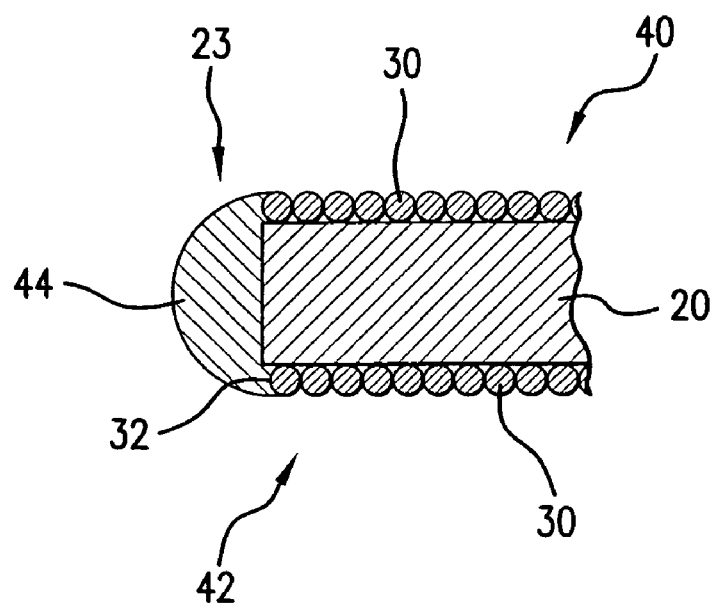
FIG. 4 is a sectional view of a forward portion of an elongated body having a solid core, according to one embodiment of this invention.

FIG. 1 shows one embodiment of medical instrument 10 that has a solid core 20. FIG. 4 shows a sectional view of a forward portion of body 40, wherein core 20 is solid. Solid core 20 may be constructed of one material or any suitable composite material. In one embodiment of this invention, core 20 is constructed of an annealed stainless steel. Any suitable metal and/or non-metal material can be used to manufacture or construct core 20.

Medical instrument 10 having solid core 20 is preferably used to provide physical therapy to an inaccessible skin surface, or even an accessible skin surface. Medical instrument 10 can be operated by reciprocating or otherwise moving body 40, preferably but not necessarily in a direction generally parallel to a longitudinal access of body 40. With such movement, the overall irregular outer surface formed by coil 30 provides a scratching effect when body 40 contacts the skin surface, during movement of medical instrument 10. With the coil helix, it is possible to rotate or roll body 40 to achieve fine or graduated positioning and manipulation of the distal end of medical instrument 10, such as along a longitudinal axis of body 40.

As shown in FIG. 1, medical instrument 10 further comprises handle 55. As shown in the embodiment of FIG. 1, open-looped end 43 of body 40 forms handle 55. Any other suitable handle can be either integrated with or attached with respect to body 40. Preferably but not necessarily, handle 55 is positioned opposite tip portion 42 of body 40.

Figure 5:
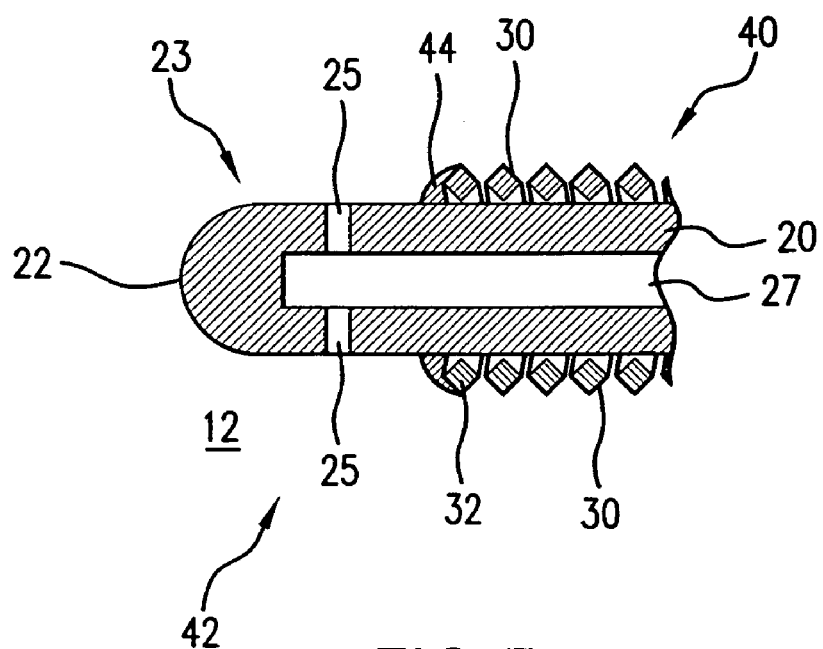
FIG. 5 is a sectional view of a forward portion of an elongated body having a hollow core, according to another embodiment of this invention.

The wire or other material that forms coil 30 can have different cross section configurations. For example, as shown in FIG. 4, the material forming coil 30 has a circular cross section and as shown in FIG. 5, the material forming coil 30 has a rectangular cross section. The material forming coil 30 can have any other suitable non-circular cross section, such as a square, a rectangle, a polygon, or can have any other suitable irregular shape. Preferred cross sections avoid sharp edges and/or burrs that could cut or penetrate a skin surface.

In addition to the cross section configuration, coil 30 can have different design parameters, such as different pitches, different coil turns per unit length and/or inconsistent heights or thicknesses or widths. For example, coil 30 shown in FIG. 4 has more turns per unit length than coil 30 shown in FIG. 5. Many different design parameters can be changed to accommodate different scratching effects, as produced by noninvasive medical instrument 10.

As shown in FIGS. 2 and 3, medical instrument 10 has a hollow core 20 which forms channel 27. One embodiment of channel 27 is shown in FIG. 5. Channel 27 can have any suitable cross section. Embodiments of medical instrument 10 having hollow core 20 can be used to provide physical therapy, as discussed with respect to solid core 20, but can also be used to deliver a medicine or drug, such as to an inaccessible area.

As shown in FIGS. 2 and 5, end 32 of coil 30 is fixedly secured to core 20 at a defined distance from end or end portion or free end 22 of core 20, for example to expose free end portion 23 of core 20. With the hollow core 20 embodiment, free end portion 23 of core 20 has at least one void 25 in communication with channel 27. Each void 25 forms communication between channel 27 and surrounding environment 12.

Also as shown in FIGS. 2 and 3, fluidic supply 50 is attached with respect to core 20, preferably but not necessarily opposite tip portion 42. In one embodiment of this invention, fluidic supply 50 comprises any suitable syringe 52 that can be used to deliver a fluidic drug or medicine from syringe 52, through channel 27, through each void 25 and into environment 12.

As shown in FIGS. 2 and 5, end 32 of coil 30 is fixedly secured to core 20, such as with a plasma-arc welding process. Resultant bead or globule 44 of the welding material forms a smooth securement of coil 30 with respect to core 20. The securement is preferably burrless.

FIG. 3 shows another embodiment of medical instrument 10 having hollow core 20. End 32 is fixedly secured to core 20 at a distance from free end 22 of core 20. In the embodiment shown in FIG. 3, end or end portion or free end portion 23 of core 20 has an enlarged outer diameter that approximately corresponds to an outer diameter of coil 30, to form a relatively smooth transition between free end portion 23 and coil 30.

In the embodiment shown in FIG. 2, void 25 is formed by a through bore within a wall of core 20. In the embodiment shown in FIG. 3, void 25 is formed by a through slot within a wall of core 20. Any other suitably shaped bore or other void can be used to form communication between channel 27 and ambient environment 12, at tip portion 42 of body 40. In one embodiment of this invention, a swab or other similar medicine applicator can be mounted or housed within void 25. The swab can then be carried, delivered or otherwise provided to an inaccessible area, for example to apply a topical numbing agent.

With the combination of core 20 and coil 30, noninvasive medical instrument 10 of this invention can be used to easily access areas that are otherwise inaccessible with many other noninvasive medical instruments and/or fingers or hands of a patient, a therapist or a doctor. The combination of core 20 and coil 30 provides an overall structure that is rigid, flexible and safely abrasive.

According to one embodiment of this invention, in a method for manufacturing noninvasive medical instrument 10 wound flexible coil 30 is positioned about core 20 and thereby forms elongated body 40. End 32 of coil 30 is fixedly secured to core 20. Rounded tip portion 42 is formed at an end, an end portion or a free end portion of elongated body 40.

Coil 30 of this invention can be formed by controlling deflection of a wire about an arbor, preferably a relatively short arbor. Medical instrument 10 can be ultrasonically cleaned to remove contaminants introduced during the manufacturing process.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A noninvasive medical instrument comprising:
a core and a flexible outer coil surrounding said core forming an elongated body, said body having a rounded tip portion, a handle one of integrated with and attached with respect to said body, said handle positioned apposite said rounded tip portion, said handle formed by an open-looped end of said elongated body and said open-looped end positioned opposite said rounded tip portion.

2. A noninvasive medical instrument according to claim 1, wherein said core is solid.

3. A noninvasive medical instrument according to claim 1 wherein an end of said coil is fixedly secured to said core.

4. A noninvasive medical instrument according to claim 3, wherein said end is plasma-arc welded to said core and said rounded tip portion is formed by a resultant bead of welding material.

5. A noninvasive medical instrument according to claim 1, wherein said rounded tip portion is burrless.

6. A noninvasive medical instrument according to claim 1, wherein said core is hollow.

7. A noninvasive medical instrument according to claim 6, wherein an end of said coil is fixedly secured to said core at a distance from a free end of said core to expose a free end portion of said core, and said free end portion of said core has at least one void in communication with a channel formed by said hollow core and an ambient environment surrounding said free end portion.

8. A noninvasive medical instrument according to claim 7, wherein said coil is plasma-arc welded to said core and a resultant bead of welding material forms a smooth securement of said coil with respect to said core.

9. A noninvasive medical instrument according to claim 8, wherein said securement is burrless.

10. A noninvasive medical instrument according to claim 7, wherein said at least one void is formed by a wall of said core having a through bore.

11. A noninvasive medical instrument according to claim 7, wherein said at least one void is formed by a wall of said core having a through slot.

12. A noninvasive medical instrument according to claim 6, further comprising a fluidic supply connected with respect to said hollow core, and said fluidic supply in communication with and delivering fluid to said channel of said hollow core.

13. A noninvasive medical instrument according to claim 12, wherein said fluidic supply comprises a syringe.

14. A noninvasive medical instrument according to claim 1, wherein said core is of annealed stainless steel.

15. A noninvasive medical instrument according to claim 1, wherein said coil is of stainless steel.

16. A method for scratching a skin surface, comprising:
selecting a noninvasive medical instrument comprising a core and a flexible outer coil surrounding said core forming an elongated body wherein said body has a rounded tip portion; and
moving the body and contacting the skin surface with said outer coil, wherein said core is solid.

17. A method for scratching a skin surface, comprising:
selecting a noninvasive medical instrument comprising a core and a flexible outer coil surrounding said core forming an elongated body wherein said body has a rounded tip portion; and
moving the body and contacting the skin surface with said outer coil, wherein said core is hollow and is used to deliver a fluid through said hollow core to the skin surface.

18. A method for scratching a skin surface, comprising:
selecting a noninvasive medical instrument comprising a core and a flexible outer coil surrounding said core forming an elongated body wherein said body has a rounded tip portion; and
moving the body and contacting the skin surface with said outer coil, wherein a handle is one of integrated with and attached with respect to said body opposite said rounded tip portion, wherein said handle is formed by an open-looped end of said elongated body.

* * * * *